United States Patent
Van Amstel et al.

[11] Patent Number: 5,170,037
[45] Date of Patent: Dec. 8, 1992

[54] SCANNING DEVICE FOR OPTICALLY SCANNING A SURFACE ALONG A LINE

[75] Inventors: Willem D. Van Amstel; Joseph L. Horijon, both of Eindhoven, Netherlands

[73] Assignee: U.S. Philips Corp., New York, N.Y.

[21] Appl. No.: 642,249

[22] Filed: Jan. 16, 1991

[30] Foreign Application Priority Data

Jan. 16, 1990 [NL] Netherlands .......................... 9000100

[51] Int. Cl.$^5$ .............................................. H01J 3/14
[52] U.S. Cl. ..................... 250/235; 250/561
[58] Field of Search ............... 250/234, 235, 236, 560, 250/561, 562, 563, 571, 572; 356/375, 376, 430, 431; 358/482, 483; 359/216, 217, 218, 219

[56] References Cited

U.S. PATENT DOCUMENTS

| | | | |
|---|---|---|---|
| 3,787,107 | 1/1974 | Sick et al. .............................. | 250/234 |
| 3,995,110 | 11/1976 | Starkweather ....................... | 359/217 |
| 4,116,566 | 9/1978 | Sick ...................................... | 356/431 |
| 4,295,743 | 10/1981 | Sick ...................................... | 356/431 |
| 4,872,757 | 10/1989 | Cormack et al. ................... | 356/376 |

Primary Examiner—David C. Nelms
Assistant Examiner—John R. Lee
Attorney, Agent, or Firm—William L. Botjer

[57] ABSTRACT

An optical scanning device comprises an optical system for imaging a part of the surface (10) to be scanned on the detection system (22–25; 122–125). The optical system comprises an objective system (43) and two cylindrical lenses (41, 42) and/or two systems of cylindrical mirrors (141a, 141b, 142a, 142b). In the direction in which the cylindrical lenses (41, 42) have their optical power, the objective system (43) functions as an imaging lens so that a light-intensive and spatial image of the surface is formed at the detection system (22–25). Due to the achieved large numerical aperture, the image formed can also be observed three-dimensionally so that information about the profile of the surface can be obtained by means of the scanning device.

12 Claims, 5 Drawing Sheets

SCANNING DEVICE FOR OPTICALLY SCANNING A SURFACE ALONG A LINE

BACKGROUND OF THE INVENTION

The invention relates to a scanning device for optically scanning a surface along a line, which device comprises a radiation-sensitive detection system for detecting radiation originating from the surface, and further an optical system for imaging an area of the surface on the radiation-sensitive detection system and a deflection system for selecting said area of the surface to be scanned, said optical system comprising a first and a second cylindrical sub-system, the first cylindrical sub-system being arranged proximate and parallel to the line to be scanned and the second cylindrical sub-system being arranged proximate to the detection system. A device of this type is used for inspecting the surface of an object, for example for reading marks which are present on this object. Such a device is also used for inspecting products such as an electronic circuit to check whether the components arranged on this circuit are present in their correct positions.

A device of the type described in the opening paragraph is known from U.S. Pat. No. 3,787,107. This Patent describes a device with which the surface of an object which is present on a conveyor belt is scanned for reading the information in the form of marks such as letters provided on the object. A line on the surface is scanned by means of a light spot, using a laser beam and a deflection system in the form of a rotating polygon mirror. The presence of the light spot selects areas of the line. The radiation reflected by the surface is subsequently projected on a photo-electric converter via two cylindrical systems in the form of cylindrical lenses. The output signal of the photo-electric converter, or the radiation-sensitive detection system is a measure of the reflection coefficient of the surface and hence of the presence or absence of a mark.

The known device measures the quantity of radiation, and hence the reflection coefficient, of the area on the surface which is illuminated by the radiation beam. However, the known device is not suitable for performing other measurements, notably for determining the relief of the surface by measuring the profile along the line to be scanned. Such a profile measurement is particularly advantageous when inspecting articles having a surface varying in height such as, for example an electric circuit whose components must be arranged in fixed positions on a flat supporting plate, or marks which are distinguished from their background in height but not in colour.

SUMMARY OF THE INVENTION

It is one of the objects of the invention to provide a device with which a three-dimensional inspection can be performed by way of an optical process. To this end the scanning device according to the invention is characterized in that the deflection system is arranged in the radiation path between the first and the second cylindrical sub-system and in that the optical system also comprises an imaging lens which is arranged in such a manner that, viewed transversely to the scanning direction, the surface is imaged in the imaging lens by the first cylindrical sub-system and the imaging lens is imaged on the detection system by the second cylindrical sub-system. If the imaging lens were absent, the point of intersection of a nominal surface with the optical axis of the optical system would be imaged correctly on the detection system as viewed transversely to the scanning direction. In the other view no image is formed at all. Other points, in the plane but next to the optical axis or at a different depth would be imaged with considerable aberrations. In the presence of the imaging lens an image is formed in the first place, as viewed in the scanning direction. Viewed transversely to the scanning direction, the imaging lens functions as a field lens which corrects aberrations in the plane as well as the depth transformation so that the portion of the surface around the nominal scanning point is spatially displayed at the detection system, which display exhibits only little aberration. The field is also enlarged considerably and vignetting is obviated. The part of the surface which is actually imaged is determined by the position or the setting of the deflection system.

It has been found that an imaging lens imaging the surface on the detection system has a more favourable effect with respect to reducing aberrations than a real field lens which images the two cylindrical sub-systems exactly on each other.

The imaging lens may be a single lens, but it may be alternatively a system composed of a plurality of lens elements.

The presence of the first cylindrical lens has the further advantage that deviations from the desired scanning line due to imperfections of the deflection system are reduced to a very large extent.

The cylindrical sub-systems comprise, for example cylindrical lenses. An attractive embodiment is characterized in that at least one cylindrical sub-system comprises a hollow cylindrical mirror. A reflecting system can be realised with a numerical aperture which is considerably larger than the numerical aperture of a lens. This provides the possibility of receiving radiation which originates from the surface and extends at an angle of more than 45° to the normal of the surface.

This embodiment is preferably characterized in that the cylindrical mirror has an elliptical shape. A good image is obtained by choosing an ellipse one focus of which is located in the nominal position of the surface and the other focus is located in the imaging lens. Moreover, an elliptic cylindrical mirror can be manufactured relatively easily by means of a milling machine.

When cylindrical lenses are used, the scanning device is characterized in that the first and second cylindrical sub-systems comprise cylindrical lenses having a refractive surface which deviates from a circular shape (aspherical cylindrical lens). With these lenses the points located on the axis of the system can be imaged without substantially any image errors. The aberrations in the images of points which are not located on the axis are reduced by the imaging lens.

A device according to the invention is further characterized in that the imaging lens is arranged in the radiation path between the deflection system and the second cylindrical sub-system. As a result, the direction of the radiation beam traversing the imaging lens is independent of the position of the deflection system. The lens and the optical light path are therefore simpler.

The width across which the surface can be scanned is limited because the optical path between different points of the line to be scanned and the detection system may not differ or may at most differ to a small extent only. This means that the deflection system must be far remote from the surface and that said width must be considerably smaller than the focal length of the imaging lens. To obviate this drawback, the scanning device according to the invention is characterized in that the optical system also comprises a correction system which is arranged in the radiation path between the first cylindrical sub-system and the deflection system so that the optical distance between the area to be scanned and the radiation-sensitive detection system is substantially independent of the adjustment of the deflection system. The scanning device according to the invention is preferably further characterized in that the correction system is composed of at least two curved mirrors arranged one after the other in the radiation path. With the aid of such a system, in which one mirror has a convex, preferably hyperbolical shape and the second mirror has a concave, preferably parabolical shape, the surface can be scanned telecentrically, while the principal axis of the scanning beam always extends at the same angle, for example, perpendicularly to the surface to be scanned. Such a correction system is described in EP-A-0,351,011 which corresponds to Ser. No. 379,514 filed Jul. 13, 1990which belongs to the prior art according to Articles 54(3) EPC. However, the scanning device described in this Application does not comprise first and second cylindrical sub-systems as in the scanning device according to the present Application. The effects and advantages of the present invention, such as forming a spatial image and the large numerical aperture and hence a considerable reception of radiation in the direction transverse to the scanning direction, so that height measurement is possible, are not described in said Application. The correction system described in said Application provides the possibility of telecentrically scanning the surface over a large width and with great accuracy.

The scanning device according to the invention may be further characterized in that the imaging lens is an anamorphotic lens. The lens system constituting the imaging lens fulfills two functions. As described in the foregoing, the imaging lens is used for correcting the imaging errors of the cylindrical systems in the direction transverse to the scanning direction and for enlarging the field. Moreover, this lens system forms an image of the surface to be scanned on the detection system in the scanning direction, in which direction the cylindrical systems do not have any power. When an anamorphotic lens is used, the two functions are optimised independently of each other.

A preferred embodiment of the scanning device according to the invention is further characterized in that the first and second cylindrical sub-systems are arranged symmetrically with respect to the imaging lens. In a symmetrical system the second cylindrical sub-system compensates for the image errors introduced by the first cylindrical sub-system. A further advantage is that only one shape of cylindrical lens or cylindrical mirror is required. It has been found that a qualitatively good image can be obtained with such a structure.

An embodiment of the scanning device according to the invention is further characterized in that the radiation-sensitive detection system comprises at least one radiation-sensitive detector preceded by a lens system, the principal axis of said lens system extending at an angle to the principal axis of the second cylindrical sub-system. Since the optical system provides a real spatial image of the surface and the cylindrical lens or the cylindrical mirror has a relatively large numerical aperture in the direction transverse to the scanning direction, the detection system may be implemented in such a manner that a triangulation method is used with which information about the height of the selected area is obtained. A double triangulation measurement is preferred because it is less sensitive to shadows and because it provides more accurate information.

A preferred embodiment of the device according to the invention is characterized in that the optical system is used entirely or partly for focusing the supplied radiation beam on the surface and in that the deflection system is also used to cause a radiation spot thus formed to move across the line to be scanned. The area to be scanned can be selected accurately by exposing the area with the aid of a small radiation spot which moves along with the area to be scanned. The optical system which is already present in the scanning device is eminantly suitable for forming such a small radiation spot on the surface. Further advantages of the use of the optical system in this case are that the incident radiation beam is incident in the same direction, for example perpendicular to the surface, as the direction in which the radiation originating from the surface is received so that a shadow effect will hardly play any role. The incident radiation beam may traverse the entire optical system or only the part between the deflection system and the surface. In the latter case the radiation beam is coupled in, for example via a mirror.

An embodiment of the scanning device according to the invention may be further characterized in that the radiation-sensitive detection system is adapted to detect a plurality of points on the surface, which points follow juxtaposed parallel paths during scanning. The surface is thereby simultaneously scanned along a plurality of lines, and hence it is scanned faster.

These and other, more detailed aspects of the invention will be described and explained in greater detail with reference to the following embodiments and the description.

BRIEF DESCRIPTION OF THE DRAWING

The drawings show a number of embodiments.

DETAILED DESCRIPTION OF THE PREFERRED EMBODIMENTS

Figure 1A:
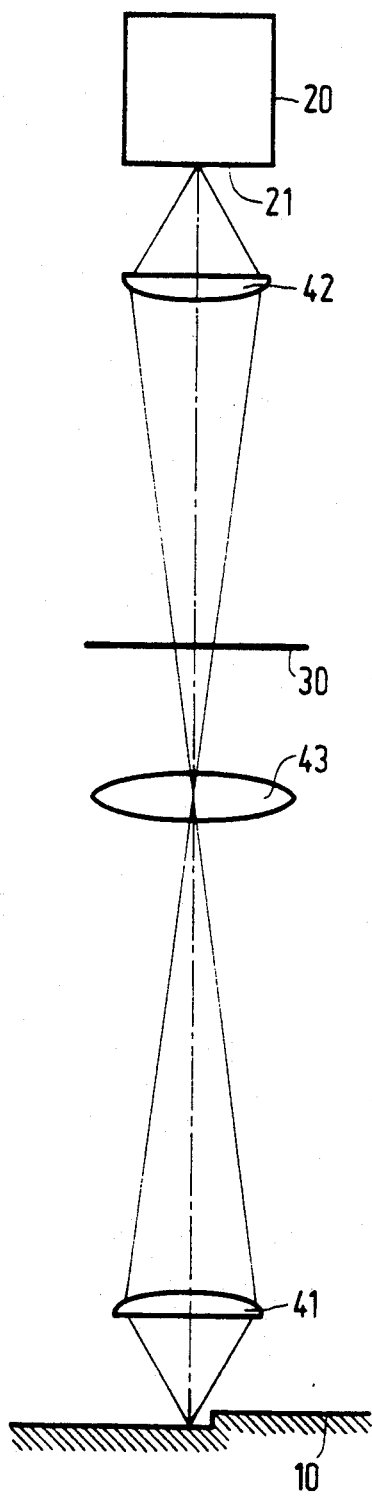
FIGS. 1a and 1b show diagrammatically the optical system of a scanning device according to the invention.
Figure 1B:
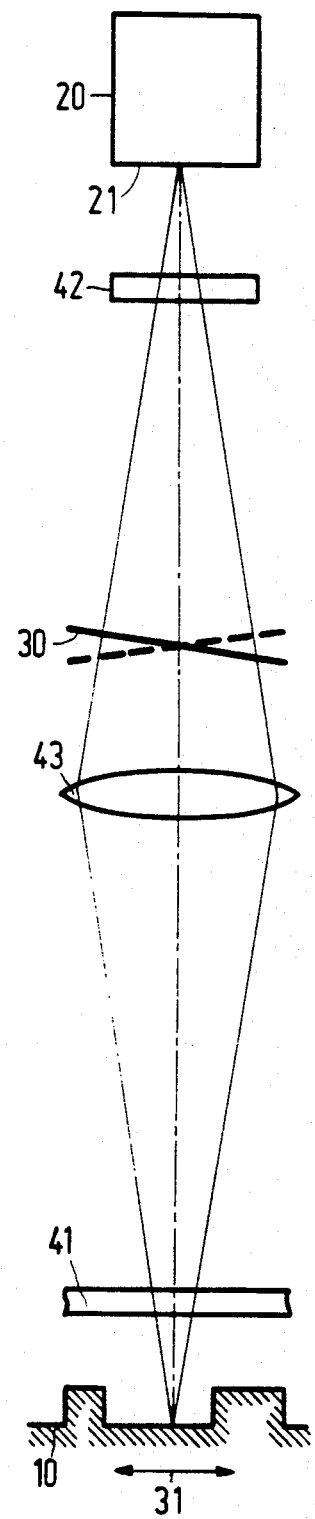

FIGS. 1a and 1b show diagrammatically the scanning device according to the invention. FIG. 1a is a side elevation in which the scanning direction is perpendicular to the plane of the drawing and FIG. 1b is a front elevation in which the scanning direction is shown in the plane of the drawing and is denoted by the double-headed arrow 31.

A part of the surface 10 is imaged proximate to a detection system 20 having a detection plane 21 by means of an optical system which comprises two cylindrical lenses 41 and 42 and an objective system 43. The cylindrical lenses are arranged in such a way that in the direction transverse to the scanning direction the image formed by the first cylindrical lens of the nominal position of the surface to be scanned substantially coincides with the image of the detection plane 21 formed by the second cylindrical lens 42. The imaging lens 43 is arranged at the position of these images. The imaging lens 43 reduces imaging errors which would otherwise be present in the images of points around the point of intersection of the optical axis with the nominal position of the surface to be scanned. Due to this implementation of the optical system, the optical system in the direction transverse to the scanning direction has a large numerical aperture and hence a relatively large resolving power and a large light output. In this case it is possible to place the detection system and the surface to be scanned relatively far apart so that space is created for the deflection system 30 with which the surface 10 is scanned along a line. It also provides the possibility of implementing the detection system 20 as a height-measuring system so that the relief of the surface 10 can be measured. The deflection system 30 is, for example a mirror rotating about an axis, such as a galvanometer mirror or a rotating polygon, or an acousto-optical element.

The imaging system 43 also forms an image of the scanned area in the scanning direction. The combination of the cylindrical lenses 41 and 42 and the imaging system 43 renders a scanning retro-image realisable in practice. The light-intensive real image which is formed at the location of the detection system 20 can be observed by means of a triangulation method or another height-measuring method so that not only the reflection differences but also the height differences of the surface 10 are detected. The imaging lens 43 may be anamorphotic so that the power is optimised, both in the scanning direction and in the direction transverse thereto.

Figure 2A:
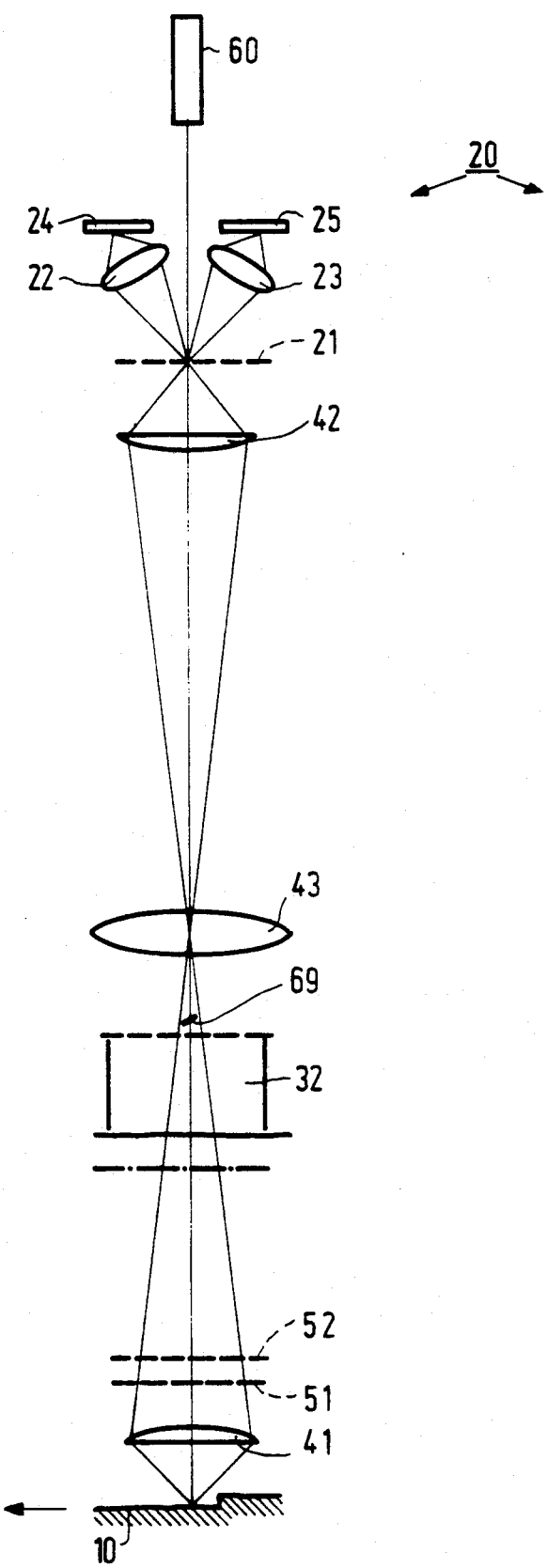
FIGS. 2a and 2b are side and front elevations of a scanning device according to the invention in which the radiation path is folded out.
Figure 2B:
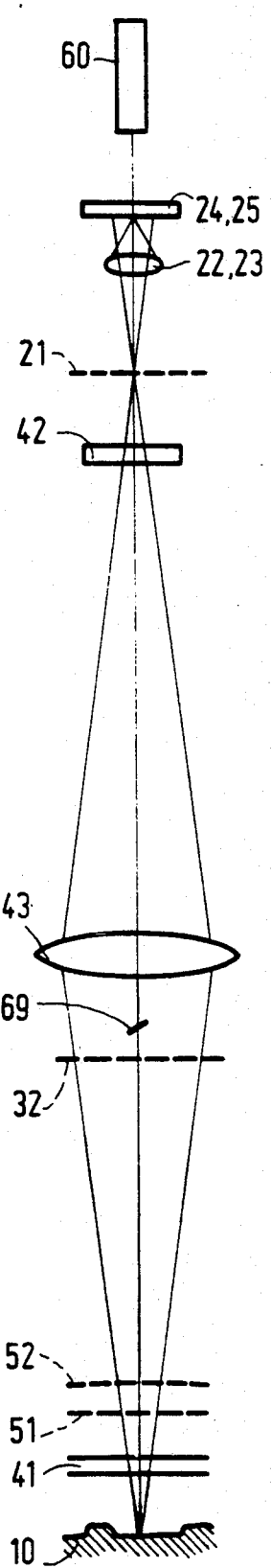

FIGS. 2a and 2b show practical embodiments of a scanning device according to the invention. In this embodiment the deflection system is a rotating polygon mirror 31 which is arranged between the objective system or the imaging lens 43 and the first cylindrical lens 41. The position of the deflection system between these two lenses means that, independent of the adjustment of the deflection system, the radiation beams always traverse the objective system 43 in the same direction so that the system need not be designed for radiation beams in different directions.

In order that the optical distance between the objective system 43 and the surface 10 remains constant in that case, the scanning device also comprises a pair of correction mirrors 51 and 52. These correction mirrors extend the radiation path between the objective system and the surface in such a way that the length of the radiation path is independent of the position of the polygon mirror 31. Moreover, the correction system does not have any net optical power so that the focal length of the optical system remains equal. Furthermore, the correction system provides the possibility of telecentrically scanning the surface 10 so that shadow effects caused by an oblique radiation beam are obviated to a maximum possible extent. The correction system is preferably composed of a first convex mirror 51 having a hyperbolic-cylindrical shape and a second concave mirror 52 having a parabolic-cylindrical shape. In the case of a small scanning width the use of circular cylinders may sufficiently approximate the most desired shape. The correction system is further described in the aforementioned EP-A-0,351,011 to which reference is made for more detailed information.

In the embodiment shown the surface may be evenly exposed by means of a light source, for example, a lamp arranged in the vicinity of the line to be scanned. In the case of such an illumination a large part of the surface is imaged on the detection system. To obtain a satisfactory display of the surface, it is necessary to use a detection system which comprises one small detector or a plurality of small detectors.

The height of a point on the surface can be measured by exposing the surface with a very small radiation spot. In principle, this radiation spot may be projected on the surface by means of a separate optical system. However, this requires a complicated control system for synchronising the movement of the radiation spot with the scanning by the scanning device. Such a control system is not required when the optical system with which the surface 10 is imaged on the detection system 20 is also used for exposing the surface. The deflection system 30 or 31 then simultaneously serves for exposing a point on the surface and for selecting the area surrounding the exposed point.

The device as shown in FIGS. 2a and 2b shows a light source unit 60, for example a laser. If necessary, the light source unit is provided with an optical system so that a radiation spot is formed in the imaginary detection plane 21. This radiation spot is then imaged on the surface 10 via the optical system comprising the elements 42, 43, 52, 51 and 41. In an alternative embodiment the incident radiation beam can also be coupled in from aside by means of a mirror at the position 69.

The radiation reflected by the surface is passed in the reverse direction to the detection plane 21 where it is projected on the position-sensitive radiation detectors 24 and 25, for example via the objectives 22 and 23. These position-sensitive radiation detectors provide an output signal which does not only indicate the intensity of the radiation incident thereon but also the position of the radiation spot on the radiation-sensitive surface. Such a detector comprises, for example a number of separate elements or a position-sensitive photodiode (PSD). Since the principal axes of the lenses 22 and 23 extend at an angle to the principal axis of the cylindrical lens 42, and hence to the principal axis of the optical system, a triangular measurement is performed by measuring the position where radiation is incident on the detectors 24 and 25. As a result the spatial position of the image of the exposed part of the surface and hence the height of this part of this surface can be determined. The large number of measurements performed when scanning the line provides a height profile of the surface along said line.

FIGS. 2a and 2b show two objectives 22 and 23 and two detectors 24 and 25. As compared with a single objective system with a detector, this provides a more accurate measurement and the influence of shadow effects in the case of steep height differences is smaller.

The light source unit 60 may be implemented in such a way that not only a single point on the surface 10 but also a number of juxtaposed points is exposed. These points may be shifted with respect to each other in the direction transverse to the scanning direction so that scanning of a surface proceeds noticeably faster than with a single exposed point. The detection system should of course be adapted to the detection of the larger number of irradiated points. A larger part of the surface may also be exposed and a number of small detectors may be used so that more juxtaposed points can be detected.

An indication of the height of (parts of) the surface may be alternatively obtained by means of a confocal detection method. In this case a punctiform light source and a punctiform detector are both imaged on the same point, which point is located in a nominal position on or near the surface to be scanned.

Other existing height measurement principles may also be used, such as interferometric, Foucault and astigmatic methods. The large numerical aperture of the scanning device provides this possibility.

Figure 3A:
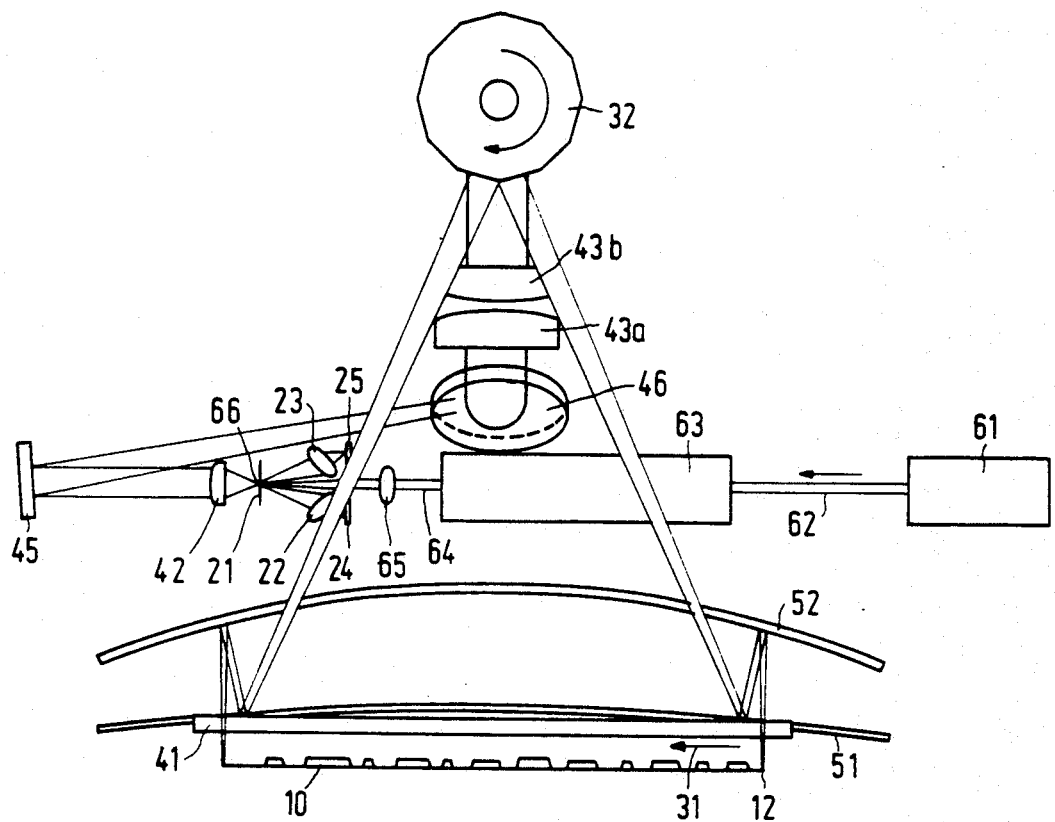
FIGS. 3a and 3b are front and side elevations of an embodiment of the scanning device according to the invention.
Figure 3B:
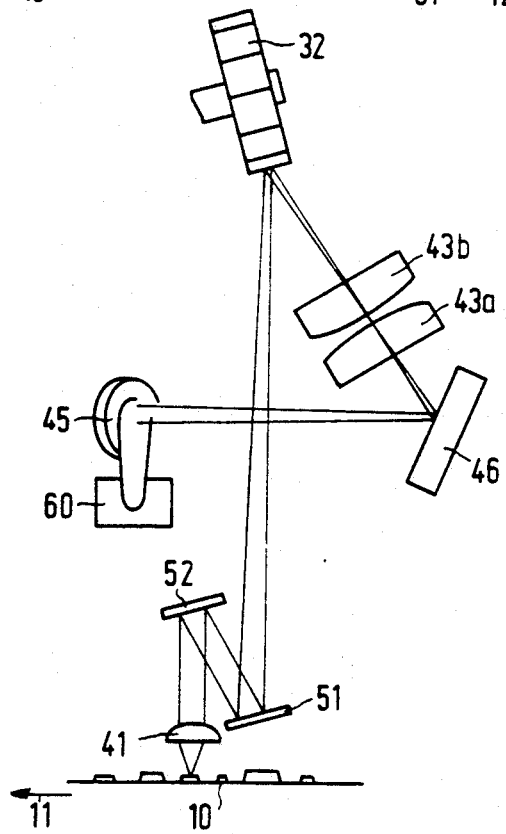

FIGS. 3a and 3b show the structure of a scanning device according to the invention with reference to an embodiment for scanning PCBs (printed circuit boards).

The radiation source unit comprises a laser 61 which generates a collimated laser beam 62. This beam may be passed through an electro-optical modulator 63 for adapting the light intensity to the detector used. The laser beam 62 is incident on a lens 65 which focuses the beam in a focus 66 in the imaginary plane 21. The laser beam then traverses the second cylindrical lens 42, is reflected on the folding mirrors 45 and 46, traverses the imaging lens or system comprising the lenses 43a and 43b and is deflected via the rotating polygon mirror 32 in the direction of the surface 10 to be scanned. The correction mirrors 51 and 52 are arranged between the polygon 32 and the surface 10 to be scanned. Ultimately the laser beam forms a scanning spot 12 on the surface 10 which scanning spot moves in the direction of the arrow 31 over the surface due to the rotation of the polygon mirror 32. The radiation reflected from the surface traverses the optical system in the reverse direction and forms an image on or near the imaginary plane 21. This image is observed by means of the detection system which comprises the lenses 22 and 23 and the detectors 24 and 25.

As is shown in FIG. 3b, the entire surface 10 is scanned by moving the PCB in the direction of the arrow 11, transverse to the scanning direction.

Figure 4:
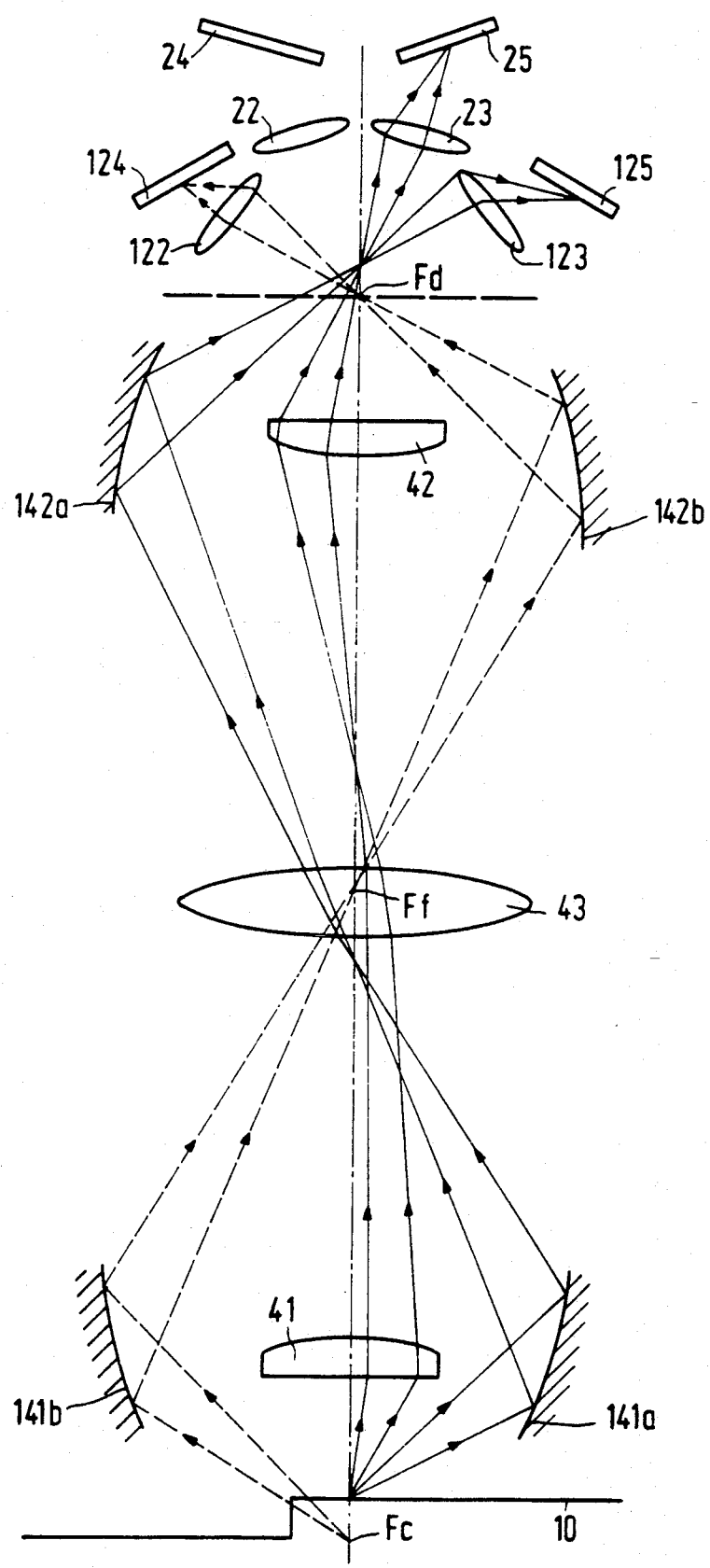
FIG. 4 is a side elevation of an embodiment in which elliptic mirrors are used.

Instead of or in addition to the cylindrical lenses 41 and 42, cylindrical mirrors may be used alternatively. This is illustrated in FIG. 4. This Figure can be compared with FIG. 2a. In FIG. 4 cylindrical mirrors 141a, 141b, 142a and 142b are arranged in addition to the cylindrical lenses 41 and 42. The reflecting surfaces of the mirrors 141a and 141b, proximate to the surface to be scanned, form parts of an ellips one focus FO of which is located at the point of intersection of the optical axis of the system and the nominal position of the surface to be scanned and the second focus Ff is located in the centre of the imaging lens 43. The second cylindrical mirror system 142a and 142b also has an elliptical shape one focus Ff of which coincides with the centre of the imaging lens and the other focus Fd is located in the detection plane 21.

The cylindrical mirrors 141a and 141b provide the possibility of receiving the radiation from the surface 10 through a large angle. This improves the resolving power of the scanning device as compared with a scanning device using a cylindrical lens 41 only. To utilise this better resolution, the detection system further comprises extra position-sensitive detectors 124 and 125 preceded by objective lenses 122 and 123. The Figures further show the radiation paths of radiation from the surface, received via the cylindrical lens 41 or via the cylindrical mirrors 141a and 141b. For radiation originating from the surface to be scanned, when it is in the nominal position, a radiation path is also shown (in a broken line). Such elliptic mirrors can be made, for example by means of a milling machine with a rotating milling cutter, in which the axis around which the milling cutter rotates extends at an angle to the direction of movement of the workpiece.

Figure 5:
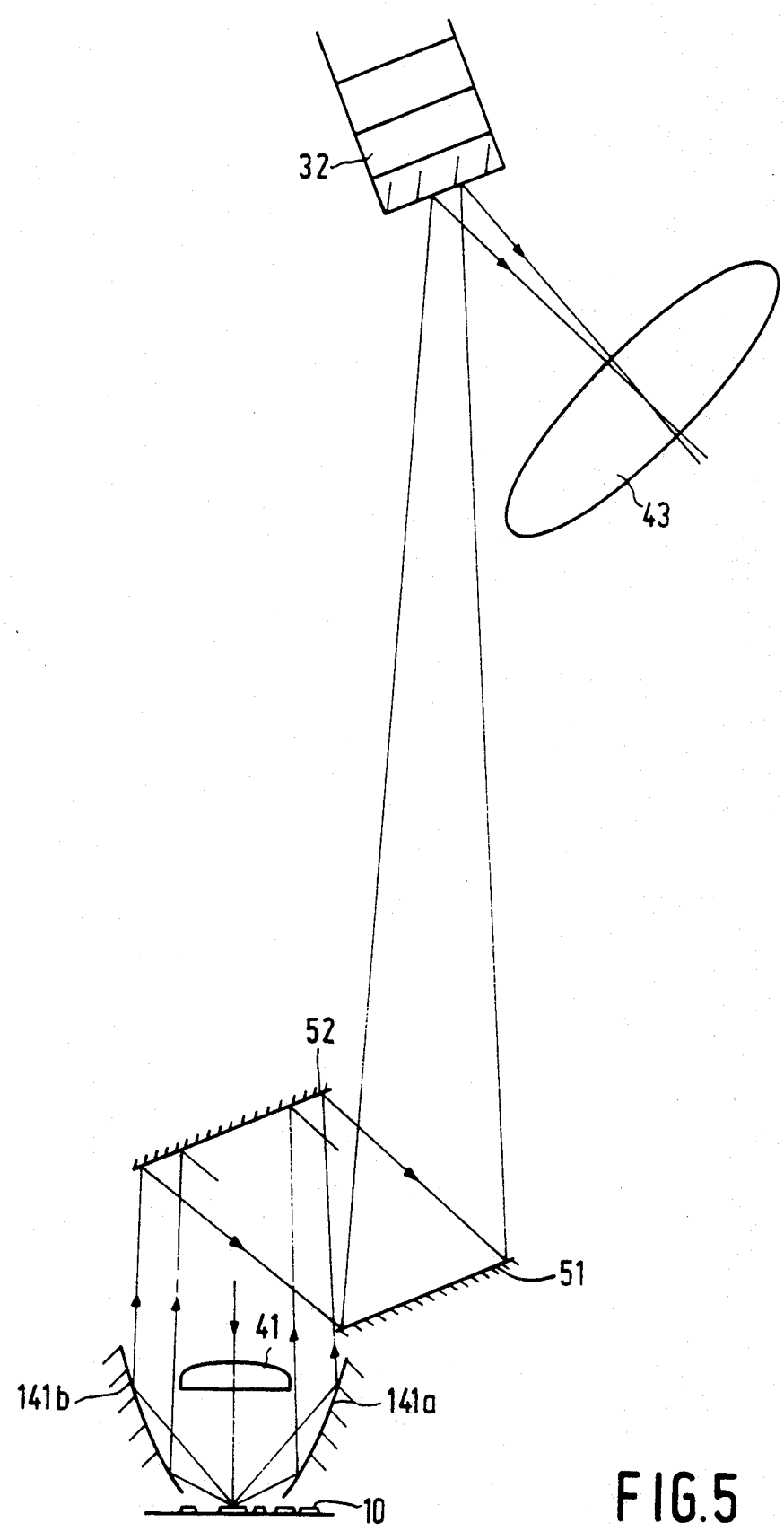
FIG. 5 shows the use of a correction system together with the elliptic mirrors.

FIG. 5 shows the position of the correction mirrors 51 and 52 when cylindrical mirrors 141a and 141b are used for receiving light. The mirrors 51 and 52 are slightly wider than in a scanning device in which only a cylindrical lens 41 is present. After reading the foregoing, a further description of the elements and their functions in this Figure may be dispensed with.

The scanning device according to the invention is not only used for inspecting (three-dimensional) objects but may also be used for exposing surfaces with a pattern, for example during the manufacture of printed circuit boards and other patterns which are made with the aid of a light-sensitive layer.

We claim:

1. A scanning device for optically scanning a surface along a line, compring a radiation-sensitive detection system for detecting radiation originating from the surface, an optical system for imaging an area of the surface on the radiation-sensitive detection system and a deflection system for selecting said area of the surface to be scanned, said optical system having a first and a second cylindrical sub-system the first cylindrical sub-system being arranged proximate and parallel to the line to be scanned and the second cylindrical sub-system being arranged proximate to the detection system, wherein the deflection system is arranged in the radiation path between the first and the second cylindrical sub-system and in that the optical system also includes an imaging lens which is arranged in such a manner that, viewed transversely to the scanning direction, the surface is imaged in the imaging lens by the first cylindrical sub-system and the imaging lens is imaged on the detection system by the second cylindrical sub-system.

2. A scanning device as claimed in claim 1, wherein the at least one cylindrical sub-system comprises a hollow cylindrical mirror.

3. A scanning device as claimed in claim 2, wherein the cylindrical mirror has an elliptical shape.

4. A scanning device as claimed in claim 1, wherein the first and second cylindrical sub-systems comprise cylindrical lenses having a refractive surface which deviates from a circular shape.

5. A scanning device as claimed in claim 1, wherein the imaging lens is arranged in the radiation path between the deflection system and the second cylindrical sub-system.

6. A scanning device as claimed in claim 4, wherein the optical system also includes a correction system which is arranged in the radiation path between the first cylindrical sub-system and the deflection system so that the optical distance between the area to be scanned and the radiation-sensitive detection system is substantially independent of the position of the deflection system.

7. A scanning device as claimed in claim 6, wherein the correction system is composed of at least two curved mirrors arranged one after the other in the radiation path.

8. A scanning device as claimed in claim 1, wherein the imaging lens is an anamorphotic lens.

9. A scanning device as claimed in claim 1, the first and second cylindrical sub-systems are arranged symmetrically with respect to the imaging lens.

10. A scanning device as claimed in claim 1, wherein the radiation-sensitive detection system comprises at least one radiation-sensitive detector preceded by a lens system, the principal axis of said lens system extending at an angle to the principal axis of the second cylindrical sub-system.

11. A scanning device as claimed in claim 1, wherein the device also includes a radiation source unit for supplying a radiation beam, the optical system is arranged entirely or partly for focusing the supplied radiation beam on the surface and the deflection system is also arranged to cause a radiation spot thus formed to move across the line to be scanned.

12. A scanning device as claimed in claim 1, wherein the radiation-sensitive detection system is adapted to detect a plurality of points on the surface, which points follow juxtaposed parallel paths during scanning.

* * * * *